(12) United States Patent
Atkinson

(10) Patent No.: US 7,225,671 B2
(45) Date of Patent: Jun. 5, 2007

(54) FLUID-QUANTITY GAUGING

(75) Inventor: Harry Atkinson, Berkshire (GB)

(73) Assignee: Smiths Group PLC, London (GB)

( * ) Notice: Subject to any disclaimer, the term of this patent is extended or adjusted under 35 U.S.C. 154(b) by 13 days.

(21) Appl. No.: 11/090,212

(22) Filed: Mar. 28, 2005

(65) Prior Publication Data

US 2005/0217367 A1 Oct. 6, 2005

(30) Foreign Application Priority Data

Apr. 3, 2004 (GB) .................................. 0407656.8

(51) Int. Cl.
*G01F 23/28* (2006.01)
*G01F 23/00* (2006.01)

(52) U.S. Cl. ..................... 73/290 V; 73/149; 73/290 R

(58) Field of Classification Search .............. 73/290 V, 73/290 R, 290 B, 149
See application file for complete search history.

(56) References Cited

U.S. PATENT DOCUMENTS 4,815,323 A 3/1989 Ellinger et al.
4,996,656 A 2/1991 Hedrick
5,900,535 A 5/1999 Doe
2002/0101373 A1 8/2002 Dickey et al.

FOREIGN PATENT DOCUMENTS

| BB | 2795818 | 1/2001 |
|----|---------|--------|
| GB | 2309524 | 7/1997 |
| WO | WO-98-09139 | 3/1998 |

OTHER PUBLICATIONS

International Search Report No. GB0505449.9, dated May 27, 2005, 1 pg.
French Search Report No. FR 0503033, dated Oct. 30, 2006, 2 pages.

*Primary Examiner*—Hezron Williams
*Assistant Examiner*—Rodney Frank
(74) *Attorney, Agent, or Firm*—Connolly Bove Lodge & Hutz LLP

(57) ABSTRACT

An ultrasonic fuel-gauging system has several probes each having a transducer mounted at the lower end of a still well. The transducers are connected to a processor, which measures the height of fuel above the transducers within the still wells. The processor also measures the resonant frequency of each transducer and from this calculates fuel density. The system calculates the mass of fuel in the tank from the density and the volume as calculated from the heights.

11 Claims, 2 Drawing Sheets

FLUID-QUANTITY GAUGING

BACKGROUND OF THE INVENTION

This invention relates to fluid-quantity gauging.

In some applications, such as aircraft fuel-gauging systems, it is necessary to determine the mass of fluid present, not just its height or volume. In such applications it is usual to measure the height at several locations, calculate the volume from knowledge of the shape of the tank, and then to compute the mass of fluid present using an indication of density. In ultrasonic gauging systems the indication of density may also be used in the height computation because the velocity of ultrasonic energy in fluid varies with its density. The indication of density may be provided by a densitometer mounted within the tank. Whilst the densitometer can provide an accurate indication of density it can only provide this indication at the location of the densitometer. There can be considerable variation in density due to temperature variation within the fluid (temperature stratification) or other physical conditions, such as variations in water content or chemical composition of the fluid at different heights.

BRIEF SUMMARY OF THE INVENTION

It is an object of the present invention to provide an alternative fluid-quantity gauging system and method.

According to the present invention there is provided a fluid-quantity gauging system including a plurality of acoustic transducer assemblies mounted for immersion in a fluid, and processing means arranged to energize the transducer assemblies and to receive outputs from the transducer assemblies, the processing means being arranged to derive from the transducer assemblies signals indicative of density at a plurality of locations within the fluid and signals indicative of height of fluid at a plurality of locations whereby the mass of fluid can be calculated.

The processing means may be arranged to determine the resonant frequency of some at least of the transducer assemblies, the processing means being arranged to derive the signals indicative of density from the resonant frequency. The signals indicative of height of fluid and the signals indicative of density may be derived from the same transducer assemblies. Alternatively, the signals indicative of height of fluid and the signals indicative of density may be derived different from different ones of the transducer assemblies. The transducer assemblies providing the signals indicative of density are preferably located adjacent those providing the signals indicative of height and may be connected in parallel with the transducer assemblies providing the signals indicative of height. The transducer assemblies providing the signals indicative of height are preferably each located at the lower end of a respective still well. The transducer assemblies providing the signals indicative of density are preferably mounted at different heights, the processing means being arranged to model the variation of density with height and to use this in the calculation of the mass of the fluid.

An aircraft fuel-gauging system according to the present invention, will now be described, by way of example, with reference to the accompanying drawings.

DETAILED DESCRIPTION OF THE PREFERRED EMBODIMENTS

Figure 1:
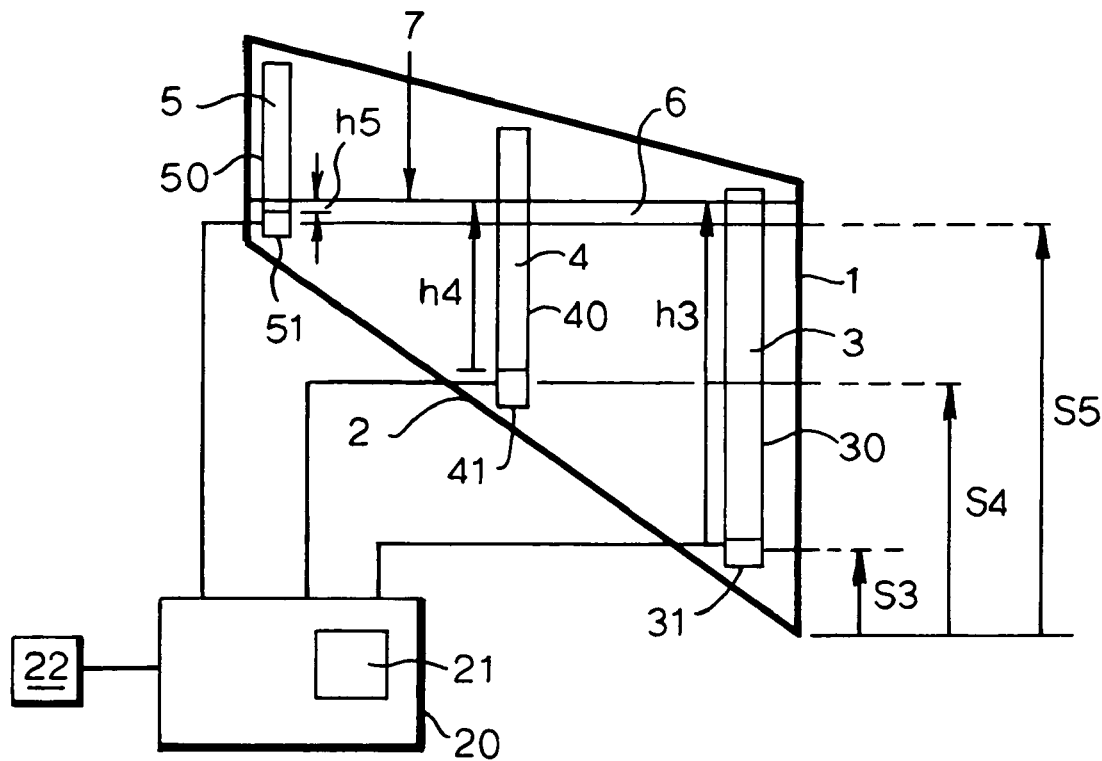
FIG. 1 shows the system schematically.

With reference first to FIG. 1, there is shown an aircraft fuel tank 1 having an inclined floor 2 and containing three ultrasonic, acoustic height measurement probes 3, 4 and 5 located in different regions of the tank. Each probe 3 to 5 includes a tubular still well 30, 40 and 50 mounted to project substantially vertically upwards from the floor 2 and a piezoelectric ultrasonic transducer assembly 31, 41 and 51 mounted within the still well at its lower end. The still well 30 to 50 is open so that it is filled with fuel to the same height as fuel 6 in the tank. Each transducer 31 to 51 is mounted so that it is immersed in any fuel present and so that, when energized, it transmits a burst of ultrasonic energy upwardly along the still well 30 to 50. When the burst of energy meets the fuel/air interface at the fuel surface 7, a major part of the energy is reflected back down the still well 30 to 50 where it is incident on the transducer 31 to 51 and produces an output signal. The time between transmission of the energy and reception of its reflection is an indication of the height of fuel.

Figure 2:
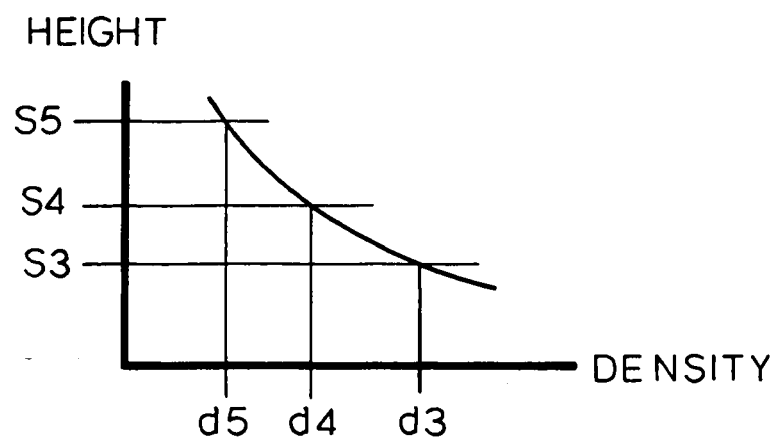
FIG. 2 is a graph illustrating variation in density with height.

The transducers 31 to 51 in each probe 3 to 5 are connected with a processing unit 20, which is arranged to energize the probes and calculate the height h3, h4 and h5 of fuel 6 at each probe 3, 4 and 5 respectively. The processing unit 20 is also arranged to measure the resonant frequency of each transducer assembly 31 to 51. The processing unit 20 includes a store 21 containing a look-up table relating resonant frequency to density and, using this, it determines the density d3, d4 and d5 at the transducer assembly 31 to 51 in each probe 3, 4 and 5 respectively. The processing unit 20 then produces a model of the variation in density d with height S of the kind shown in FIG. 2. The processing unit 20 uses this information both in calculations of fuel height, to compensate for variations in acoustic velocity with density, and in calculating the total mass of fuel after determining its volume. In this way, the accuracy of measurement of fluid mass can be improved without the need for separate densitometers. The processing unit 20 provides an output representative of mass of fuel to a display or other utilisation means 22.

Figure 3:
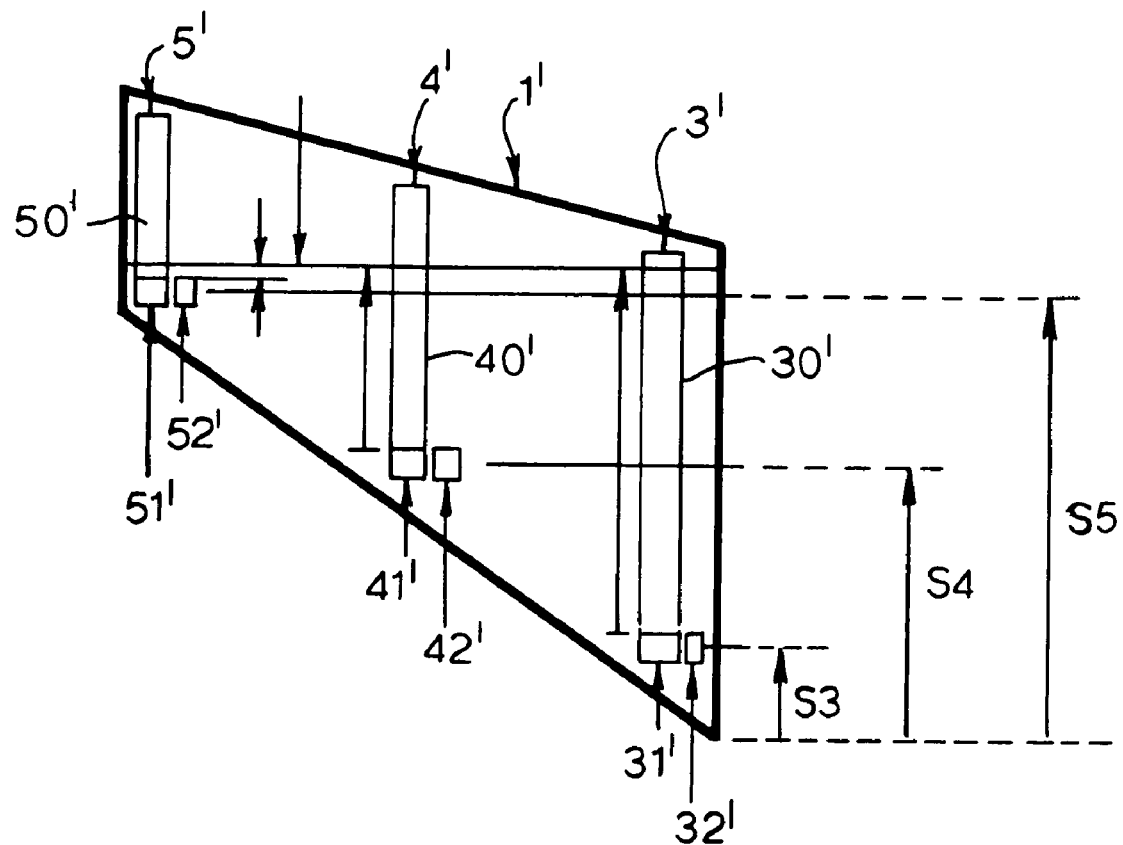
FIG. 3 shows a modification of the system of FIG. 1.

It is not essential that the same transducers used to measure fluid height be used to measure density. Instead, as shown in FIG. 3, each probe 3', 4' and 5' could have a density-measuring transducer assembly 32', 42' and 52' associated with it in addition to the height-measuring transducer assembly 31', 41 ' and 51'. The transducer assemblies 32', 42' and 52' are mounted outside the still wells 30', 40' and 50' and closely adjacent the lower end of the probe where the height-measuring transducer assemblies 31' to 51' are located, so that the density is measured as close as possible to the height-measuring transducers. However, it is not essential for the density-measuring transducer assemblies to be located adjacent the probes; they could instead be spaced from the probes.

Figure 4:
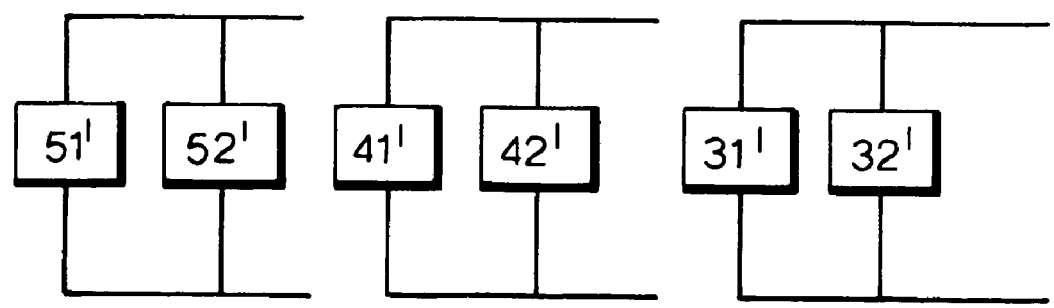
FIG. 4 illustrates interconnection of transducers in the arrangement of FIG. 3.

As shown in FIG. 4, the density-measuring transducer assemblies 32' to 52' are preferably connected in parallel with the height-measuring transducer assemblies 31' to 51' so that the supply to and from the probe assembly 3' to 5' including the density-measuring transducer can be provided along one cable. This arrangement enables two transducer assemblies of different kinds to be used, one being more suited to height measurement and the other having a greater variation in resonant frequency with density. The transducer assemblies in a parallel pair may operate at different frequencies, thereby enabling the processing unit to select between the two transducer assemblies.

It is not essential for the probes to have a still well since they could be used in an open, tubeless configuration, such as of the kind described in U.S. Pat. No. 5,670,710. In such arrangements, the height-measuring transducer assembly could be used to measure the density, or a separate transducer assembly could be used.

What I claim is:

1. A fluid-quantity gauging system comprising: a plurality of acoustic transducer assemblies mounted for immersion in a fluid, and a processor arranged to energize the transducer assemblies and to receive outputs from the transducer assemblies, wherein the processor is arranged to determine the resonant frequency of at least some of the transducer assemblies and derive from the resonant frequency signals indicative of density at a plurality of locations within the fluid, and wherein the processor is arranged to derive signals indicative of height of fluid at a plurality of locations, whereby the mass of fluid is calculated.

2. A fluid-quantity gauging system according to claim 1, wherein the signals indicative of height of fluid and the signals indicative of density are derived from the same transducer assemblies.

3. A fluid-quantity gauging system according to claim 1, wherein the signals indicative of height of fluid and the signals indicative of density are derived from different ones of the transducer assemblies.

4. A fluid-quantity gauging system according to claim 3, wherein the those of the transducer assemblies from which the signals indicative of density are derived are located adjacent those of the transducer assemblies from which the signals indicative of height are derived.

5. A fluid-quantity gauging system according to claim 3, wherein those of the transducer assemblies from which the signals indicative of density are derived are connected in parallel with those of the transducer assemblies from which the signals indicative of height are derived.

6. A fluid-quantity gauging system according to claim 1, wherein those of the transducer assemblies from which the signals indicative of height are derived are each located at a lower end of a respective still well.

7. A fluid-quantity gauging system comprising: a plurality of acoustic transducer assemblies mounted for immersion in a fluid, and a processor arranged to energize the transducer assemblies and to receive outputs from the transducer assemblies, wherein the processor is arranged to derive from the transducer assemblies signals indicative of density at a plurality of locations within the fluid and signals indicative of height of fluid at a plurality of locations whereby the mass of fluid can be calculated, and wherein those of the transducer assemblies from which the signals indicative of density are derived are mounted at different heights, and wherein the processor is arranged to model the variation of density with height and to use the variation of density with height in the calculation of the mass of the fluid.

8. A fluid-quantity gauging system comprising: a plurality of acoustic probes, each probe including a still well mounted to project substantially vertically in fluid and an acoustic transducer at a lower end of the still well; a processor; and a connection between the processor and each transducer such that the processor can energize the transducers and receive outputs therefrom, wherein the processor is arranged to derive signals from the transducers indicative of height of fluid at a plurality of locations, and wherein the processor is arranged to determine the resonant frequency of at least one of said transducers and to derive therefrom an indication of the density of the fluid.

9. A fluid-quantity gauging system comprising: a plurality of acoustic probes, each probe including a still well mounted to project substantially vertically in fluid and an acoustic transducer at a lower end of the still well; at least one additional acoustic transducer mounted adjacent the lower end of one of said still wells; a processor; and a connection between the processor and each transducer at the lower end of the still wells such that the processor can energize the transducers and receive outputs therefrom, wherein the processor is arranged to derive signals from the transducers at the lower end of the still wells indicative of height of fluid at a plurality of locations, and wherein the processor is arranged to determine the resonant frequency of said additional transducer and to derive therefrom an indication of the density of the fluid.

10. A fluid-quantity gauging system according to claim 9, wherein the system includes a plurality of said additional transducers, wherein each said additional transducer is located at the lower end of a respective still well, and wherein the processor is arranged to determine the resonant frequency of each said additional transducer.

11. A fluid-quantity gauging system according to claim 10, wherein the additional transducers are connected in parallel with the transducers mounted at the lower end of the respective still wells.

* * * * *